(12) United States Patent
Cruse et al.

(10) Patent No.: US 10,019,879 B2
(45) Date of Patent: Jul. 10, 2018

(54) CONICAL LIGHT ABSORBER FOR SMOKE DETECTOR

(71) Applicant: Apollo Fire Detectors Limited, Hampshire (GB)

(72) Inventors: Gregory Michael Cruse, Hampshire (GB); Philip Watson, Hampshire (GB); Robert David Knight, Hampshire (GB)

(73) Assignee: Apollo Fire Detectors Limited, Hampshire (GB)

( * ) Notice: Subject to any disclaimer, the term of this patent is extended or adjusted under 35 U.S.C. 154(b) by 0 days.

(21) Appl. No.: 15/316,207

(22) PCT Filed: Jun. 16, 2015

(86) PCT No.: PCT/GB2015/051766
§ 371 (c)(1),
(2) Date: Dec. 5, 2016

(87) PCT Pub. No.: WO2015/193660
PCT Pub. Date: Dec. 23, 2015

(65) Prior Publication Data
US 2017/0162019 A1    Jun. 8, 2017

(30) Foreign Application Priority Data

Jun. 16, 2014   (GB) .................................. 1410717.1

(51) Int. Cl.
*G08B 17/10* (2006.01)
*G08B 17/107* (2006.01)
(Continued)

(52) U.S. Cl.
CPC .......... *G08B 17/107* (2013.01); *G01N 21/53* (2013.01); *G02B 5/003* (2013.01); *G08B 17/113* (2013.01); *F21V 33/0076* (2013.01)

(58) Field of Classification Search
CPC .... G08B 17/107; G08B 17/113; G01N 21/53; G02B 5/003
See application file for complete search history.

(56) References Cited

U.S. PATENT DOCUMENTS 3,316,410 A * 4/1967 Meili ................... G01N 15/065
                                                    250/565
3,361,030 A * 1/1968 Goldberg ............... G01N 21/53
                                                    250/574

(Continued)

FOREIGN PATENT DOCUMENTS

DE     102012219635    2/2014
EP         0135361     3/1982
(Continued)

*Primary Examiner* — Hoi Lau
(74) *Attorney, Agent, or Firm* — Patti & Malvone Law Group, LLC

(57) ABSTRACT

A smoke detector having a light source for generating a beam of light is disclosed. The smoke detector is arranged to transmit the beam along an optical axis and includes a sensor for receiving light scattered from the beam off the optical axis by smoke; and a light trap comprising one or more walls that define a volume for receiving light that passes unscattered from the light source past the sensor along the optical axis. The volume includes a first end closest on the optical axis to the light source; and a second end furthest on the optical axis from the light source. The volume is open at said first end but is otherwise closed, and at least one of the walls is sloped from the first end to the second end, such that the light trap progressively narrows from the first end axially towards the second end.

17 Claims, 9 Drawing Sheets

(51) Int. Cl.
*G02B 5/00* (2006.01)
*G01N 21/53* (2006.01)
*G08B 17/113* (2006.01)
*F21V 33/00* (2006.01)

(56) References Cited

U.S. PATENT DOCUMENTS

| | | | | |
|---|---|---|---|---|
| 3,874,795 A * | 4/1975 | Packham | G01N 21/53 | 250/574 |
| 4,121,110 A * | 10/1978 | Solomon | G08B 17/107 | 250/574 |
| 4,618,777 A * | 10/1986 | Schoenfelder | G08B 17/10 | 250/381 |
| 4,857,895 A * | 8/1989 | Kaprelian | G08B 17/103 | 250/208.4 |
| 4,906,978 A * | 3/1990 | Best | G08B 17/113 | 250/574 |
| 5,731,875 A * | 3/1998 | Chandler | G02B 6/4249 | 356/336 |
| 5,872,361 A * | 2/1999 | Paoli | G01N 21/534 | 250/341.8 |
| 6,057,774 A * | 5/2000 | Venzant | G08B 17/113 | 250/381 |
| 6,184,537 B1 * | 2/2001 | Knox | G01N 21/53 | 250/574 |
| 6,758,568 B2 * | 7/2004 | Valenti | G02B 5/003 | 359/601 |
| 6,914,535 B2 * | 7/2005 | Matsukuma | G08B 17/113 | 340/577 |
| 7,248,173 B2 * | 7/2007 | Yamasaki | G08B 17/113 | 340/628 |
| 7,884,731 B2 * | 2/2011 | Mizuo | G08B 17/113 | 250/574 |
| 2005/0242967 A1 * | 11/2005 | Yamasaki | G08B 17/113 | 340/630 |
| 2012/0262714 A1 * | 10/2012 | Gonzales | G01N 21/4738 | 356/338 |
| 2014/0063499 A1 * | 3/2014 | Kato | G08B 17/107 | 356/338 |

FOREIGN PATENT DOCUMENTS

| | | |
|---|---|---|
| EP | 0817338 | 1/1998 |
| EP | 1868172 | 12/2007 |
| GB | 2330410 | 4/1999 |
| GB | 2379977 | 3/2003 |
| GB | 2404731 | 2/2005 |
| JP | 2000065741 | 3/2000 |
| WO | 97/42485 | 11/1997 |
| WO | 2014/050859 | 4/2014 |

* cited by examiner

CONICAL LIGHT ABSORBER FOR SMOKE DETECTOR

FIELD

Embodiments described herein relate to a smoke detector, and in particular to a scattered-light smoke detector.

BACKGROUND

Scattered-light smoke detectors measure the amount of light scattered by an aerosol in order to infer the smoke density, and hence indicate a fire. In a typical such detector, a photo detector and a light source are mounted within a chamber into which the aerosol is admitted. A partly collimated beam of light is passed through the aerosol but not allowed to shine directly onto the photo detector. When the aerosol contains sufficient concentrations of smoke particles, the light emitted by the source is scattered by the smoke, a small portion of which will be incident on the photo detector. The output response of the photo detector is used to infer the smoke density. The amount of light incident on the photo detector, when smoke density reaches levels typical of a fire, is around $1/100,000$ to $1/10,000$ of the quantity of light emitted by the source.

The chamber's principal function is to prevent light which has not been scattered by smoke from reaching the photo detector, i.e. it must be dark. One contribution to stray light is reflections from the chamber walls. Although the walls may be black, there is still a substantial amount of reflected light compared with the levels scattered from the smoke. Reflections from the chamber walls increase with time as dust enters the chamber and coats the walls.

Another contribution to stray light is from external light. The detector must necessarily permit external air and air/smoke aerosols to reach the chamber. However, passages which allow air to flow into the chamber may also permit light to enter, for example via reflections.

In order to ensure proper function of the sensor therefore, the chamber must: allow air and air/smoke aerosols to reach the sensor; prevent significant amounts of light being reflected from the source onto the photo detector when there is no smoke present; and continue to prevent these reflections even after long term use in dusty environments.

One way of reducing the effect of reflected light is to use a light source with a narrow beam having small divergence. Granted GB patent GB2404731 discloses a surface mount device (SMD) comprising an LED chip device which produces a narrow light beam having a low divergence within a small envelope.

SUMMARY

The present invention provides a smoke detector comprising a light source for generating a beam of light and arranged to transmit the beam along an optical axis; a sensor for receiving light scattered from the beam off the optical axis by smoke; and a light trap comprising one or more walls that define a volume for receiving light that passes unscattered from the light source past the sensor along the optical axis, where said volume comprises a first end closest on the optical axis to the light source; and a second end furthest on the optical axis from the light source; wherein said volume is open at said first end but is otherwise closed, and wherein at least one of the walls is sloped from the first end to the second end, such that the light trap progressively narrows from the first end axially towards the second end.

Preferably, said light trap, when viewed from the side of the smoke detector, comprises walls which extend above and below a direction parallel to or coincident with the optical axis and walls which extend alongside said direction. For example, the light trap may be a cone, and may be a right-circular or oblique cone, whose axis is on or parallel to the optical axis. Alternatively, it may be a pyramid having opposed sloping walls above and below the optical axis, and opposed sloping walls extending alongside the optical axis.

Preferably, the walls of the light trap that extend above and below the said direction slope towards one another in the direction from the first end to the second end.

Preferably, the walls of the light trap that extend alongside the said direction slope towards one another in the direction from the first end to the second end.

Thus it is preferred to give the light trap a continuous tapering shape along the axis.

Preferably, said volume has an axis of rotational symmetry parallel to the optical axis.

The axis of symmetry may, but need not, coincide with the optical axis. It preferably intersects the second end.

The open, first end encompasses substantially the whole of the solid angle of the beam.

Preferably, the internal walls of the light trap are curved.

Preferably, the light trap is generally conical in shape.

Preferably, the light source, light detector and light trap are mounted within a chamber and the light trap projects inwards from the walls of the chamber towards the light source.

Preferably, the light detector is positioned between the light source and the light trap.

Preferably, there is an unobstructed optical path between the emitter and the light trap.

Preferably, the sensor receives directly at least a portion of the light scattered from the beam off the optical axis by smoke.

Preferably, the smoke detector comprises a generally circular disc-shaped base connected to a generally circular dome-shaped cover, containing between them a chamber layer comprising the light source, light detector and light trap, the light trap being mounted with its axis on a radius of the smoke detector, and the cover having a peripheral serpentine air inlet to allow smoke-bearing air into the chamber but to block direct light from the exterior.

BRIEF DESCRIPTION OF FIGURES

Embodiments of the invention will now be described by way of example with reference to the accompanying drawings in which.

DETAILED DESCRIPTION

Figure 1:
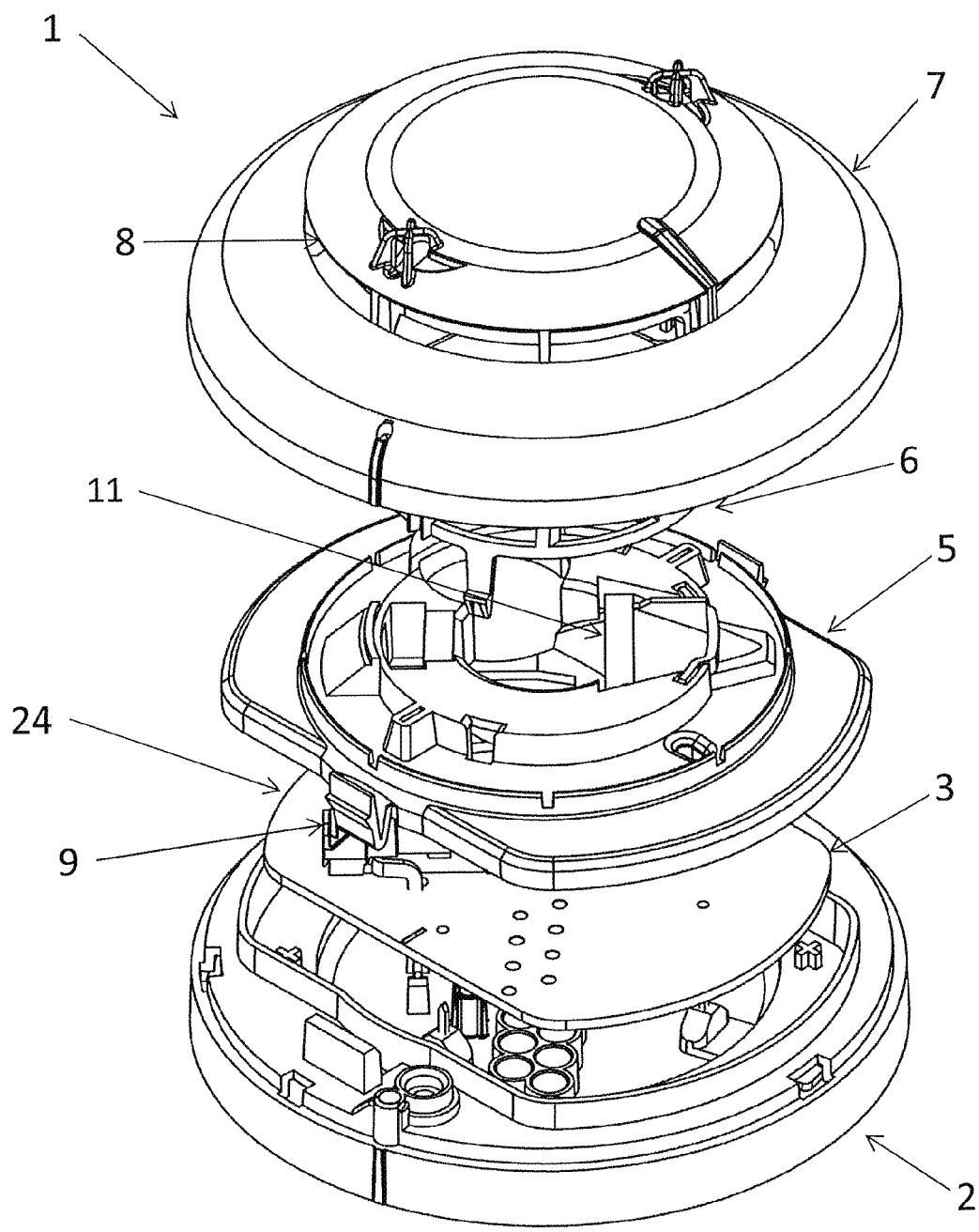
FIG. 1 shows an exploded view of a smoke detector according to an embodiment.
Figure 2:
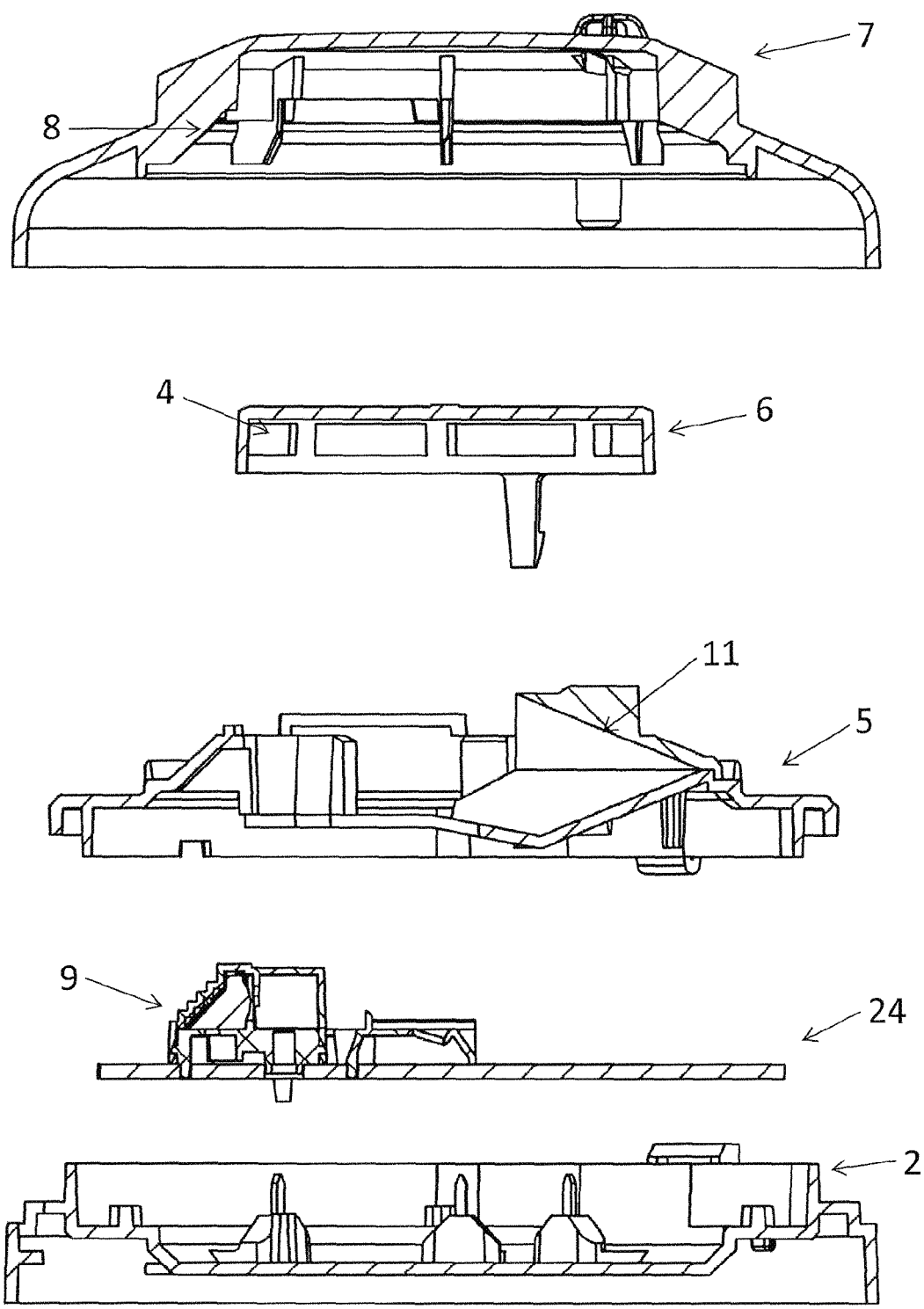
FIG. 2 shows an exploded cross-section through a smoke detector according to the embodiment of FIG. 1.

FIGS. 1 and 2 show exploded views of a smoke detector 1 according to an embodiment. The smoke detector 1 comprises a generally circular disc-shaped base 2; a cover 7 which fits on the base 1 and has generally a circular dome shape; a circuit board 24; a chamber layer 5 and a chamber cover 6. The chamber cover 6 fits on the chamber layer 5. The chamber layer 5 and the circuit board 24 have arcuate ends which follow the periphery of the base 2 and cover to fit within them; and parallel, straight sides, giving them an oval or running-track shape in plan view. The chamber cover 6 comprises vents 4. The chamber layer 5 fits on the base 2 between the cover 7 and the base 2. The circuit board 24 fits on the base 2 between the base 2 and the chamber layer 5. The cover 7 comprises an air inlet 8.

Figure 3:
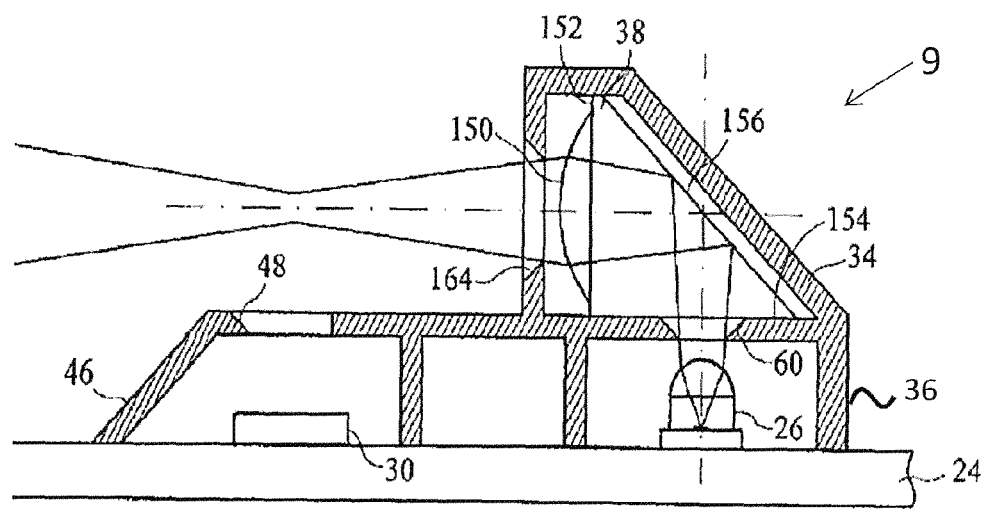
FIG. 3 shows an optical bench assembly described in granted patent GB2404731.

On the circuit board 24 is fitted an optical bench assembly 9. One example of a suitable optical bench assembly is shown in FIG. 3. The optical bench assembly comprises an SMD LED chip package 26 and a light sensor 30 fitted on the circuit board 24. Further comprised in the example of the bench assembly 9 are a prism carrier 34, a carrier base 36 and a prism 38 mounted on the carrier base 36. One part of the prism carrier 34 is formed as an arm 46 that extends above the light sensor 30.

In this embodiment, the light sensor 30 is a photodetector.

The prism 38 redirects the beam of light produced by the LED 26 so that the optical axis of the redirected beam passes over the light sensor 30. The bench assembly 9 further comprises a lens 152 which focuses the beam of light such that an image of the LED is formed directly above the light sensor 30.

When smoke particles enter the space above the light sensor 30, a portion of the light emitted by the LED is scattered towards the photo detector. The arm 46 has an aperture 48 in its base to allow light scattered from the redirected light beam to pass directly through to the light sensor 30.

The position of the sensor ensures that at least a portion of the scattered light is scattered directly, via an unobstructed optical path, towards the light sensor 30. No further reflections are required for at least this portion of the scattered light to reach the light sensor 30. This ensures that the detector remains efficient even when dust build-up has occurred within the detector. Dust can affect the ability of surfaces to reflect light and therefore this configuration ensures that, even if dust build up has occurred, the signal generated by the portion of light directly scattered towards the detector will be unaffected.

This optical bench assembly forms the basis of granted patent GB 2404731 and will therefore not be described further here.

Figure 4:
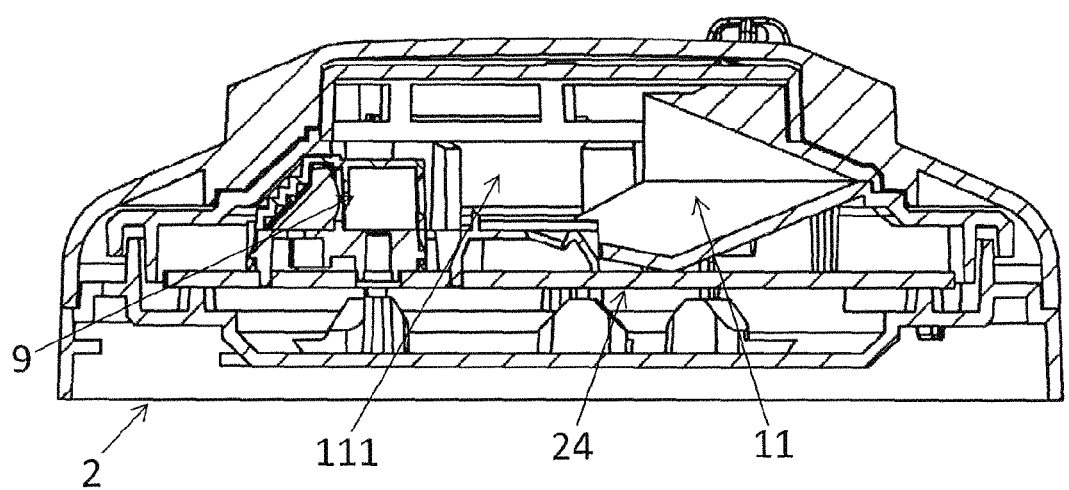
FIG. 4 shows a view of a cross-section through the assembled smoke detector of FIGS. 1 and 2.

FIG. 4 shows the assembled detector according to the present embodiment in section view. When assembled, a detection chamber 111 is formed above the bench assembly 9. Air is directed into this chamber from outside the detector through inlets 8 and vents 4. When smoke enters chamber 111, the beam of light is scattered towards the sensor, as described above. The mechanism of enabling air/smoke penetration into the chamber 111 is discussed in more detail below. In this embodiment, the chamber 111 is of broadly cylindrical construction.

Figure 5:
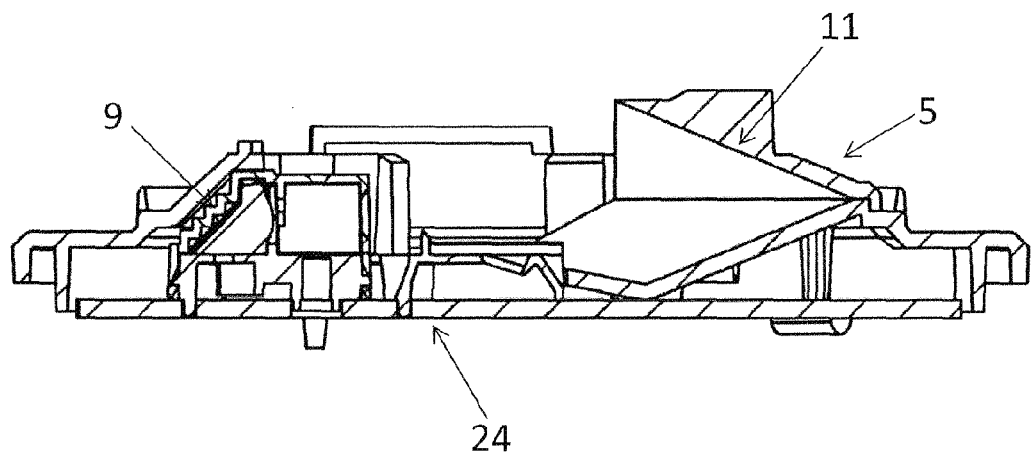
FIG. 5 shows a section view of the chamber assembly of the smoke detector of FIGS. 1 and 2.
Figure 6:
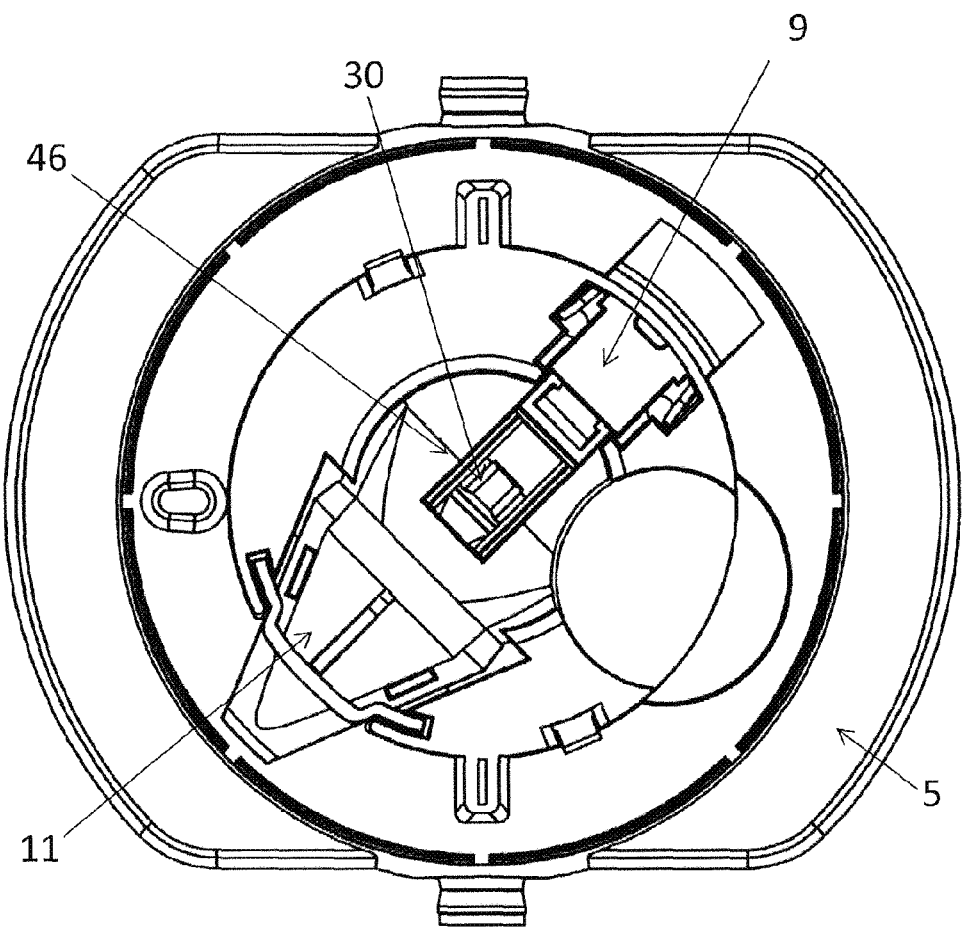
FIG. 6 shows a plan view of the chamber assembly shown in FIG. 5.

As described in relation to FIGS. 1 and 2 above, when assembled, the chamber layer 3 is fitted on to the circuit board 24. The chamber 3 comprises a hole into which the bench assembly slots. A section view of the chamber assembly according to this embodiment is shown in FIG. 5. A plan view of the assembly is shown in FIG. 6.

As described above, in order to ensure proper function of the sensor, it is necessary to prevent significant amounts of light being reflected from the source onto the photo detector when there is no smoke present within the chamber. In the embodiment of FIGS. 1, 2 and 3, this is achieved using a light dump, or light trap. A light dump according to this embodiment will now be described in detail.

The chamber layer comprises a light trap 11. When assembled, the light trap 11 is mounted radially of the detector 1 and diametrically opposite the light source contained within the bench assembly 9, as can be seen in FIGS. 5 and 6. The light detector 30, located in the arm 46 of the bench assembly 9 (see FIG. 3 and accompanying description) is positioned between the light source and the light trap.

The purpose of the light trap is to trap any light which is unscattered by smoke particles and to prevent it from being reflected around the chamber, particularly onto the light sensor. The light trap 11 acts to effectively absorb the beam of light from the bench assembly 9 preventing further reflections around the chamber. The light trap is sized such that it encompasses the majority of the beam from the light source. In this example, the diameter of the cone opening is about twice the optical beam width, and is sized such that any undesired reflections from accumulated dust particles on the prism 38 or the lens 150 that exit the bench aperture 164 are collected by the cone.

In this embodiment, there is an unobstructed optical path between the bench assembly and the light trap. This ensures that the only reflections of the beam which occur outside of the trap are due to smoke particles and not due to reflection from components within the detector. This is particularly important in dusty environments because dust build up on surfaces can alter their ability to reflect light and increase the chance of unwanted reflections towards the detector.

Figure 7:
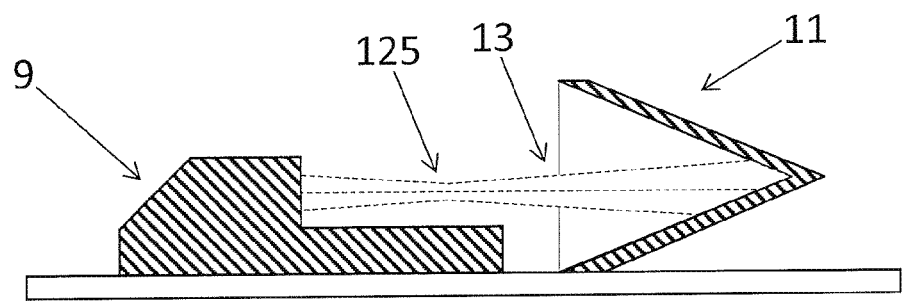
FIG. 7 shows a schematic of a section view of the chamber assembly of a smoke detector according to an embodiment.
Figure 8:
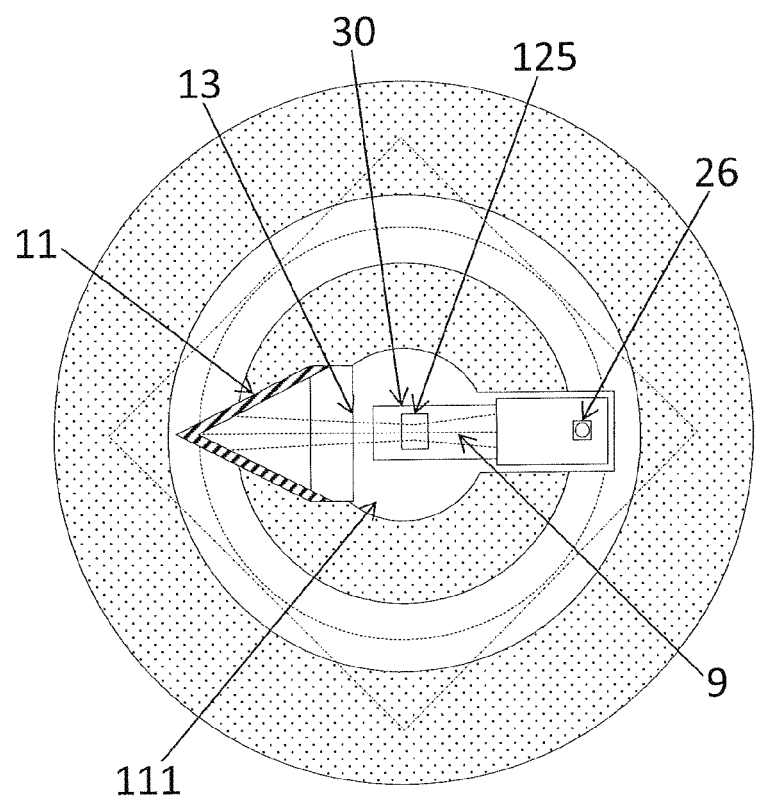
FIG. 8 shows a plan view of the chamber assembly of the smoke detector according to the embodiment.

A schematic section diagram of the light trap and bench assembly according to this embodiment is shown in FIG. 6. A schematic plan diagram of the chamber 111 is shown in FIG. 7. The position of the light trap (in this embodiment, a cone) 11 is configured such that the solid angle of the beam 13 is captured after passing over the photodiode 30. The chamber housing is generally cylindrical and the light trap is disposed radially of the detector and diametrically opposite the emitter.

In the present embodiment, the light trap 11 is a right-circular cone. This has an axis of rotational symmetry parallel to the optical axis or on it. However, other shapes may be used. The key features of the light trap are that the light trap comprises a three-dimensional surface which is open at the end which receives the beam of light but is otherwise closed. Preferably, the inner wall surface should be continuous, without transverse edges or sharp portions. The curvature may be constant or smoothly varying along the axis and/or around the axis. Further, one or more of the walls of the light trap slope from the mouth of the light trap (the open end) to the narrower, opposite end of the trap. Thus the light trap becomes narrower downstream relative to the beam. The light beam enters the light trap through the wide open end, or the mouth of the light trap, and is subsequently reflected on the internal walls of the light trap. Because the light trap has one or more walls which slope towards the narrower, downstream end of the trap, reflection on a sloping wall or walls directs the light beam forwards and further into the light trap, necessitating further reflections before the beam is able to escape from the trap. No part of the inner wall surface is angled such as to reflect the light rays from an axial direction backwards. As reflections attenuate the beam, this process reduces the amount of light which escapes into the detection chamber. Because the light trap is open only at one end, the accumulation of dust on the surfaces of the light trap are minimised.

The light trap 11 is as large as possible within the confines of the disc-shaped chamber layer 5. In this embodiment, the axial length of its internal surface is approximately one half the outer radius of the smoke detector 1. This proportion is preferably in the range 0.3 to 0.7, preferably 0.4 to 0.6.

Shapes other than a right circular cone suitable for forming the light trap include shapes which have side walls which slope towards each other or top and bottom walls which slope towards each other such as a prism or polyhedron. The walls of the trap may be flat such as a pyramid or they may be curved such as an oblique cone. The narrow end of the trap may be the apex of a generally conical shape or it may be flat such as a frustrated cone or curved such as a hemisphere. Any other shape comprising the features described in the preceding paragraph may also be employed as the light trap.

As described in relation to FIG. 3, above, the bench assembly 9 and light trap are configured such that the beam of light forms an image of the LED at point 125, in the centre of the cavity and above the light sensor located in the arm of the bench assembly. The beam of light then diverges into the light trap via an unobstructed optical path.

In this embodiment, the open end of the light trap 11 is sized such that it encompasses substantially the whole of the solid angle of the beam of light. By "substantially the whole of the solid angle of the beam of light", substantially the whole of the solid angle created by the divergence of the beam from point 125 above the sensor 30 is meant, as is shown in FIG. 7. In this embodiment, aside from the formation of the LED image and subsequent diversion of light towards the optical trap, there is no additional enlargement or condensing of the beam at any point on the optical path between the optical bench assembly and the optical trap. For example, no lens is required to focus the beam into the optical trap.

Figure 9:
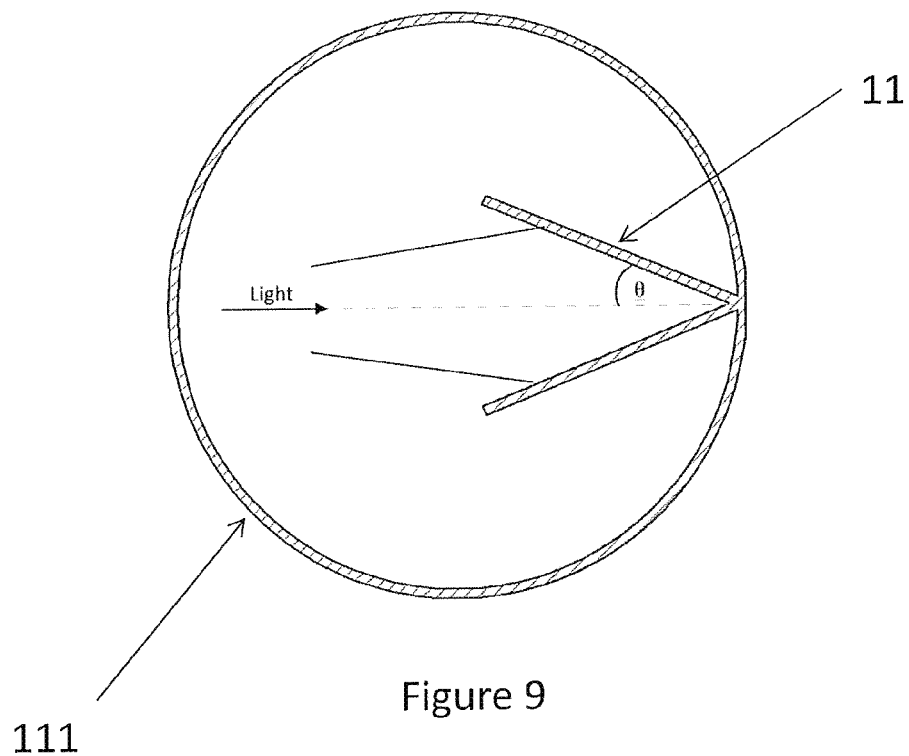
FIG. 9 shows a simplified schematic of a plan view of the chamber assembly of the smoke detector according to the embodiment.

A more simplified schematic of a plan view of a chamber according to this embodiment is shown in FIG. 9 which shows the direction of the beam of light and a cone 11. The surfaces of the cone 11 make an angle θ with the axis of the cone. The internal angle between the axis of the cone and the surface θ is chosen to maximise the number of reflections that each ray makes. In this embodiment θ is less than 45°, ensuring at least two reflections before emerging from the cone.

In an alternative embodiment, the axis of the cone is parallel to, but offset laterally from, the optical axis of the beam of light.

Figure 10:
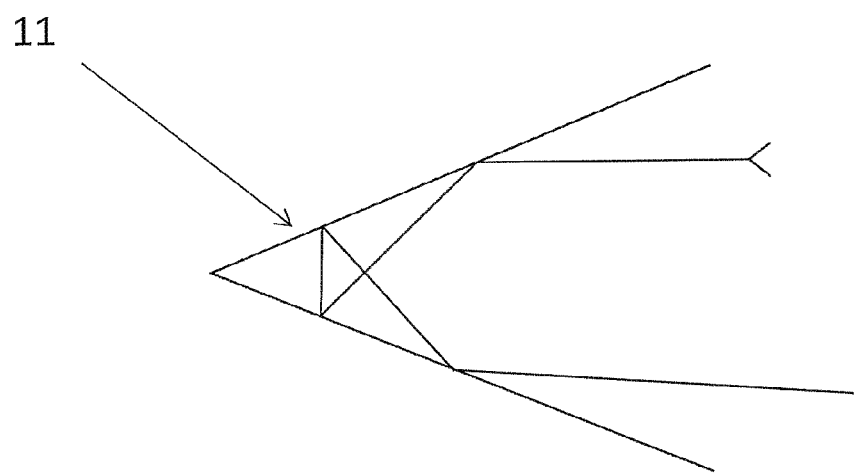
FIG. 10 shows the path of a ray of light in a light trap according to the embodiment.

For a right-circular cone, making θ 22.5° or less ensures at least four internal reflections of the beam. FIG. 10 shows the path of a single ray of light entering the cone from the light source. In this embodiment, θ=22.5° and the ray experiences 4 reflections within the cone before it leaves the cone. In the preferred embodiment, dark plastic is chosen for the internal cone surface. Preferably, each reflection attenuates more than 90% of the incident light. In this embodiment, the compound attenuation of all reflections within the cone is thus greater than 0.9999.

The cone light trap according to the above embodiments has a broad open area for receiving the beam generated within the chamber and tapers to a single apex. In an alternative embodiment, the cone is mounted slightly away from the optical axis of the beam. In an embodiment, the cone is mounted slightly above, typically by one beam diameter, the optical axis of the beam. The axis of the cone is preferably parallel to the beam axis, but small deviations are allowable. This eliminates the need for a sharp point at the apex of the cone, enabling straightforward manufacture in thermoplastics.

The simple design of the cone is easy to manufacture. The cone requires no sharp edges to achieve its performance, thereby limiting the effects of tooling wear. Further, the large mouth of the cone permits easy cleaning for limiting the effects of the accumulation of dust on the cone surfaces.

In this embodiment, the light trap is moulded. In this embodiment, the light trap is moulded from thermoplastics, advantageously polycarbonate or ABS. In this embodiment, the light trap is formed by injection moulding. The technique of injection moulding is well known in the art. In an embodiment, the light trap is moulded from dark, polished plastic. In an embodiment, the internal surface finish of the light trap is chosen so that reflections are predominantly specular (as opposed to diffuse), producing the reflection pattern shown in FIG. 10. In this embodiment the light trap is moulded in two parts. The mould tool surface is polished to a mirror surface finish.

The light trap according to embodiments described above, effectively reduces stray reflections between light source and photo detector due to its size and shape. Since its function and location is separate from the air/smoke entry, the light is subject to limited accumulated dust on its working surfaces, being open at one end only. In addition, since stray light is so effectively absorbed at the light trap, accumulation of dust on other internal chamber surfaces does not have a substantial effect on the amount of stray reflections. In product performance terms, this translates to the ability to have long usage in dusty environments before the operation of the sensor is compromised.

A light trap according to embodiments described above is compact and efficient at attenuating the unscattered light beam. The efficiency of the tapering shape at attenuating the light is such that no peripheral baffles are required in the chamber for further absorption of light. The space-efficiency of the light trap and the fact the unscattered light is captured relatively closely to the photodiode means that other components such as thermistors may be incorporated easily into the design of the smoke detector. Because the light is dealt with at the light trap, there is no risk of unwanted reflections and therefore a reduction in performance caused by the incorporation of such additional components.

Figure 11:
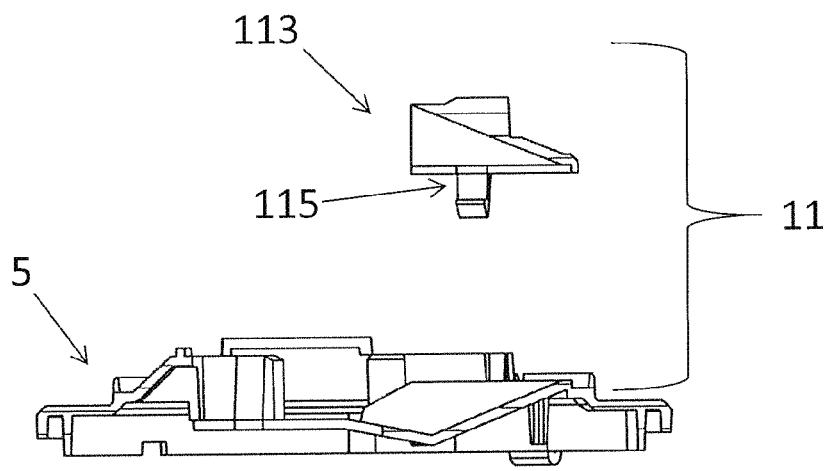
FIG. 11 shows an exploded section view of a chamber layer of a smoke detector according to the embodiment.

In this embodiment, a portion of the light trap is detachable. This is shown in FIG. 11, in which an exploded section view of the chamber layer according to the embodiment is shown. The upper portion 113 of the cone 11 is detachable for easy manufacture and cleaning. The upper portion 113 comprises legs 115 which hook into holes formed in the chamber layer 5 thereby securing it to the chamber layer 5. The lower portion of the cone 11 is formed integrally with the remainder of the chamber layer 5. Forming the cone in this way, with two halves that clip together on assembly during manufacture, simplifies production.

Although the embodiments described above employ a bench and surface mount LED and photo detector, the light dump according to the embodiments described above may equally be employed with other LED-photo detector configurations. In an alternative embodiment, the light dump is employed with a through-hole LED and/or photodetector. Such an LED has electrical leads and is horizontally mounted to emit the beam horizontally along the same optical axis.

As noted above, a second requirement of the chamber is to ensure that external light does not reach the photo detector, while permitting air and smoke to reach the light sensor.

In the embodiment of FIGS. 1, 2 and 4, this is achieved by employing a serpentine—or U-shaped—air path entry into the chamber.

Figure 12:
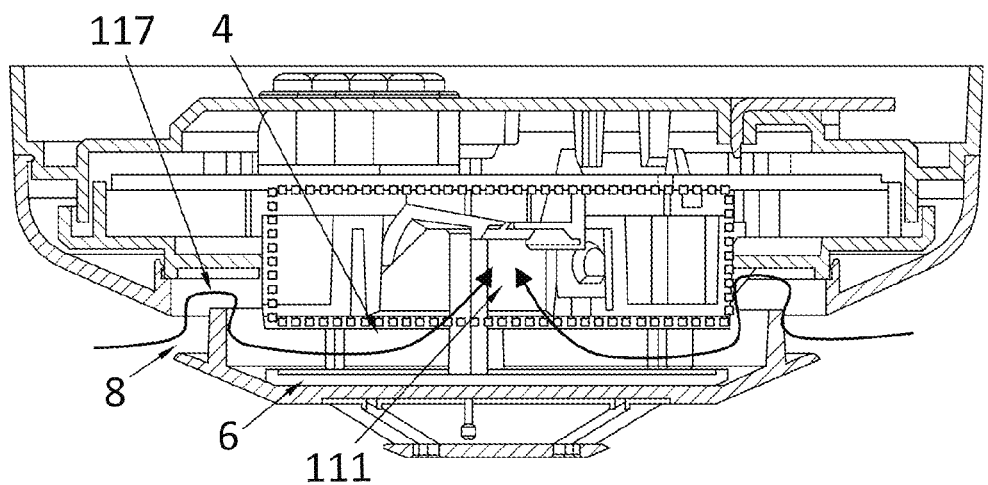
FIG. 12 shows the air entry path of a smoke detector according to the embodiment.

A schematic diagram of the air path according to the preferred embodiment is shown in FIG. 12, which shows a section view of a detector according to the embodiment. The solid arrows indicate the direction air must take in order to travel from outside of the chamber into the cavity 111. The air enters through vents 8 and is then forced into a U-shaped path 117. The air enters the chamber through the chamber cover 6, in particular through the vents 4 formed in chamber cover 6.

Figure 13:
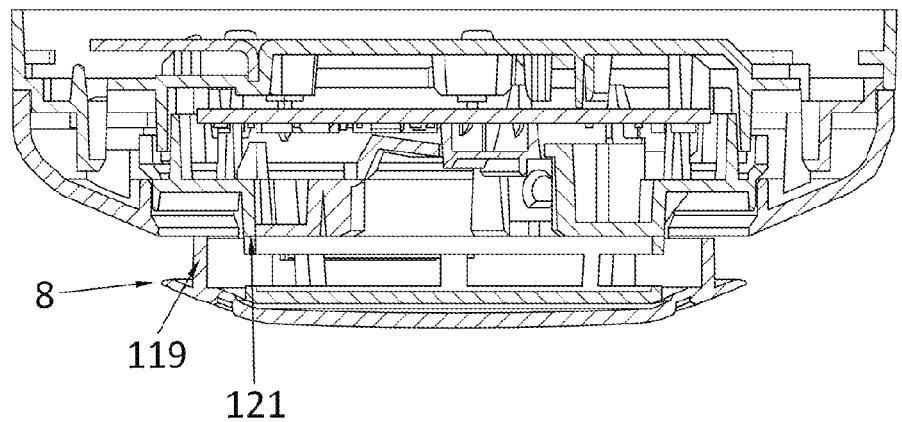
FIG. 13 shows a section view of a smoke detector according to the embodiment.

In this embodiment, the serpentine profile of the air inlet is achieved by introducing two vertical walls. These are shown in the FIG. 13, which shows a section view of a detector according to the embodiment. The first wall 119 abruptly disturbs the airflow, forcing the air to change direction and slow. The second wall 121 slows down the airflow further and is redirected towards the centre of the chamber.

Figure 14:
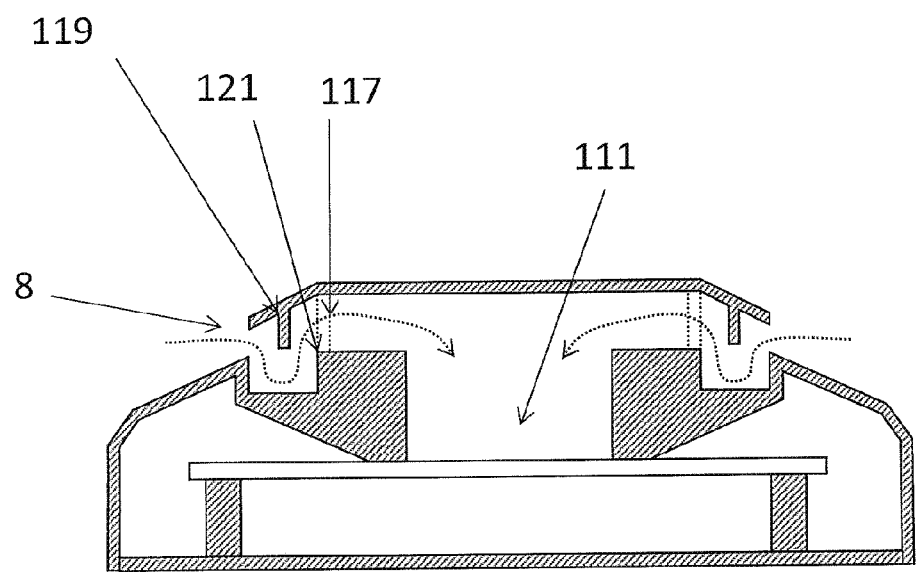
FIG. 14 shows a schematic section view of a smoke detector according to the embodiment with optical features omitted.

A schematic of the air entry path is shown in FIG. 14, which shows a section view of a detector according to the embodiment, with optical components omitted for clarity. From the figure, the path of the airflow 117 around the first and second walls 119 and 121 before entering the cavity 111 is clearly visible.

Figure 15:
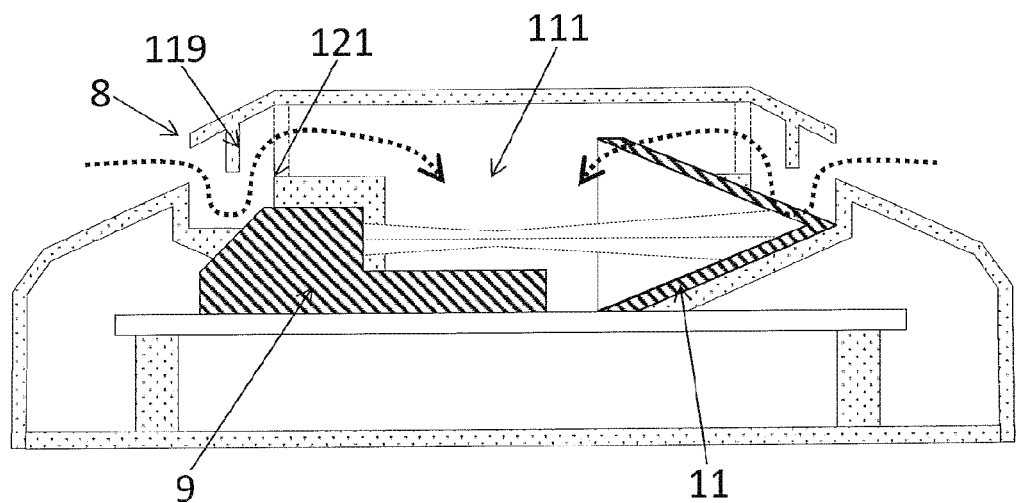
FIG. 15 shows the view of FIG. 14 with optical features included.

A further schematic, in which the optical features have been included, is shown in FIG. 15.

This arrangement of walls prevents dust from entering the chamber, thereby preventing the detector going into alarm due to accumulation of dust. When dust loaded air hits either of the walls the dust particles are deposited as they are generally larger than smoke particles. The smoke aerosol is relatively unimpeded by the serpentine. Therefore this serpentine ensures that a low quantity of dust enters the chamber, ensuring a low number of false alarms due to dust accumulation. The dimensions of the serpentine are chosen to optimise the impeding of dust whilst allowing the complete spectrum of smoke to enter the chamber. The wall 119 has a height which is a compromise between impeding dust ingress and admitting smoke. The same applies to the depth of the channel opposite the wall 119, i.e. the height of the wall 121. The geometry chosen in this embodiment provides a serpentine flow channel of approximately constant width, i.e. the air flow path is of near constant cross-section as it bends. The principal function of the mesh is to prevent the ingress of objects larger than 0.4 mm diameter, such as insects. It also prevents large dust clumps and/or fibres entering the chamber. It is important to place this after the serpentine, as the serpentine itself may contribute to the formation of large clumps of dust which could subsequently be dislodged and enter the chamber.

In an embodiment, the vents 4 of chamber cover 6 are covered with a vertical mesh.

The two-wall arrangement according to this embodiment further prevents the entry of light into the chamber. Typically, when light hits a surface and is reflected, the intensity of the light is reduced by a factor of 10. The U shaped inlet formed by the two-wall arrangement means that any light entering the chamber would typically need to reflect more than four times before reaching the chamber.

Figure 16:
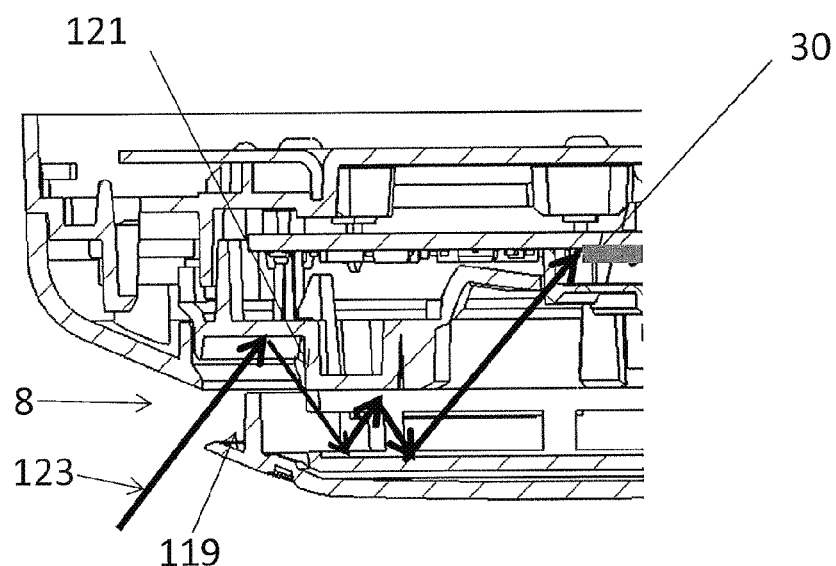
FIG. 16 shows the light entry path of a smoke detector according to the embodiment.

FIG. 16 shows the path taken by a ray of light 123 in order to reach the light sensor 30 from outside of the detector. Four reflections are taken by the light before reaching the detector.

Detectors according to embodiments described above employ both the serpentine air-path and light dump described above in combination. However, they may be employed separately. For example, in an embodiment, the light dump is employed with a design of air inlet which is different from the serpentine air-inlet. In another embodiment, the serpentine air-inlet is employed with a different light-attenuating component.

While certain embodiments have been described, these embodiments have been presented by way of example only, and are not intended to limit the scope of the invention. Indeed, the novel methods, devices and systems described herein may be embodied in a variety of forms; furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

The invention claimed is:

1. A smoke detector comprising:
   a light source for generating a beam of light and arranged to transmit the beam along an optical axis;
   a sensor for receiving light scattered from the beam off the optical axis by smoke; and
   a light trap comprising one or more walls that define a volume for receiving light that passes unscattered from the light source past the sensor along the optical axis,
   where said walls define said volume by way of:
   a first end closest on the optical axis to the light source;
   and a second end furthest on the optical axis from the light source;
   wherein said first end defines an opening to receive unscattered light;
   wherein said second end is closed, and
   wherein at least one of the walls is sloped from the first end to the second end, such that the light trap progressively narrows from the first end axially towards the second end, and wherein the open first end encompasses substantially the whole of a solid angle of the beam.

2. A smoke detector according to claim 1, wherein said light trap, when viewed from a side of the smoke detector, comprises walls which extend above and below a direction parallel to or coincident with the optical axis and walls which extend alongside said direction.

3. A smoke detector according to claim 2, wherein the walls of the light trap that extend above and below the said direction slope towards one another in the direction from the first end to the second end.

4. A smoke detector according to claim 2, wherein the walls of the light trap that extend alongside the said direction slope towards one another in the direction from the first end to the second end.

5. A smoke detector according to claim 1, wherein said volume has an axis of rotational symmetry parallel to the optical axis.

6. A smoke detector according to claim 5, wherein the axis of symmetry parallel to the optical axis does not coincide with the optical axis.

7. A smoke detector according to claim 5, wherein said axis of symmetry intersects the second end.

8. A smoke detector according to claim 1, wherein the internal wall of the light trap is curved.

9. A smoke detector according to claim 1, wherein the light trap is a cone.

10. A smoke detector according to claim 9, where the cone is a right circular cone.

11. A smoke detector according to claim 9, where the cone is an oblique cone.

12. A smoke detector according to claim 1, wherein the light trap is generally conical in shape.

13. A smoke detector according to claim 1, wherein the light source, light detector and light trap are mounted within a chamber and the light trap projects inwards from walls of the chamber towards the light source.

14. A smoke detector according to claim 13, comprising a generally circular disc-shaped base connected to a generally circular dome-shaped cover, containing between them a chamber layer comprising the light source, light detector and light trap, the light trap being mounted with its axis on a radius of the smoke detector, and the cover having a peripheral serpentine air inlet to allow smoke-bearing air into the chamber but to block direct light from the exterior.

15. A smoke detector according to claim 1, wherein the light detector is positioned between the light source and the light trap.

16. A smoke detector according to claim 1, wherein there is an unobstructed optical path between the light source and the light trap.

17. A smoke detector according to claim 1, wherein the sensor receives directly at least a portion of the light scattered from the beam off the optical axis by smoke.

* * * * *